United States Patent
Garneau, III

(10) Patent No.: US 7,734,371 B2
(45) Date of Patent: Jun. 8, 2010

(54) SYSTEM AND APPARATUS FOR DISPENSING INFORMATION AND PRODUCT

(75) Inventor: Leo J Garneau, III, Doylestown, PA (US)

(73) Assignee: McNeil-PPC, Inc., Skillman, NJ (US)

( * ) Notice: Subject to any disclaimer, the term of this patent is extended or adjusted under 35 U.S.C. 154(b) by 651 days.

(21) Appl. No.: 11/531,440

(22) Filed: Sep. 13, 2006

(65) Prior Publication Data

US 2007/0093934 A1 Apr. 26, 2007

Related U.S. Application Data

(60) Provisional application No. 60/728,849, filed on Oct. 21, 2005.

(51) Int. Cl.
*G06F 17/00* (2006.01)

(52) U.S. Cl. .................. 700/236; 700/237; 700/240; 700/241

(58) Field of Classification Search ............... 700/237, 700/241, 244, 236, 240
See application file for complete search history.

(56) References Cited

U.S. PATENT DOCUMENTS

| 5,377,864 | A | 1/1995 | Blechl et al. |
| 5,758,095 | A | 5/1998 | Albaum et al. |
| 5,907,493 | A | 5/1999 | Boyer et al. |
| 6,021,394 | A | 2/2000 | Takahashi |
| 6,529,801 | B1 * | 3/2003 | Rosenblum ............. 700/237 |
| 6,564,121 | B1 | 5/2003 | Wallace et al. |
| 6,697,704 | B2 | 2/2004 | Rosenblum |
| 6,711,465 | B2 | 3/2004 | Tomassi |
| 6,735,497 | B2 | 5/2004 | Wallace et al. |
| 6,766,218 | B2 | 7/2004 | Rosenblum |
| 6,883,681 | B1 * | 4/2005 | Coughlin et al. ......... 221/124 |
| 6,892,941 | B2 | 5/2005 | Rosenblum |
| 6,898,299 | B1 * | 5/2005 | Brooks ............... 382/115 |
| 7,006,893 | B2 | 2/2006 | Hart et al. |
| 2002/0032582 | A1 | 3/2002 | Feeney, Jr. et al. |
| 2002/0103672 | A1 | 8/2002 | Torres et al. |
| 2004/0111179 | A1 | 6/2004 | Broadfield et al. |
| 2004/0210341 | A1 | 10/2004 | Wallace et al. |
| 2004/0215369 | A1 | 10/2004 | Rosenblum |
| 2005/0049746 | A1 | 3/2005 | Rosenblum |
| 2005/0144037 | A1 | 6/2005 | Geiger |

FOREIGN PATENT DOCUMENTS

| WO | WO 98/02130 A1 | 1/1998 |
| WO | WO 01/97140 A1 | 12/2001 |

* cited by examiner

*Primary Examiner*—Gene Crawford
*Assistant Examiner*—Timothy R Waggoner
(74) *Attorney, Agent, or Firm*—Laura A. Donnelly; David Crichton

(57) ABSTRACT

The present invention is directed to a vending system or automated store and method of practice that has a means for inputting data, e.g., data input device, means for analyzing the data, e.g., microprocessor, and an output based on the analysis that includes information, product, or both. The invention is particularly suited for the delivery of healthcare and/or personal care products. The system provides a prospective consumer with information about products and their use, and preferably is capable of accessing qualified savings accounts for purposes of completing a transaction.

20 Claims, 2 Drawing Sheets

SYSTEM AND APPARATUS FOR DISPENSING INFORMATION AND PRODUCT

RELATED APPLICATION

This application claims priority from a provisional filing, U.S. Ser. No. 60/728,849, filed on Oct. 21, 2005 entitled "System and Apparatus for Dispensing Information and Product".

The present invention is directed to methods and systems for dispense information and products.

BACKGROUND

Vending machines are a well-known means for providing products to consumers without the need for a large physical storefront, significant retail space or constant presence of sales personnel. Vending machines can be located to maximize convenience for the consumer and directly managed on a periodic basis to check inventory, deposits, and general condition of the machine.

Electronic vending machines have been developed that are capable of using paper currency, coins or credit cards to process payments. Vending machines capable of transmitting information required for sales estimates to a central computer system are known, as shown in U.S. Pat. No. 6,021,394.

Consumers are accustomed to purchasing various food items, beverages and other consumables in vending machines. These consumable items are generally purchased individually from vending machines. Though less common, personal care items, usually individual unit sizes, are also available in vending machines. The option to purchase personal and/or health care products in other than individual packets would be a benefit to consumer.

Many individuals participate in health plans or programs that cover at least some of the cost of over-the-counter healthcare products. For example, health savings accounts or flexible saving accounts are offered in many plans/programs. Employees or their employer contribute sums of money towards such accounts, which can then be used for approved purposes. In many cases, a permitted purpose is to cover deductibles, co-payments or purchases of defined healthcare products that are not otherwise covered by the plan or program. A vending machine that would permit a consumer to record a purchase with a central computer containing information about their healthcare account, either in real time or at a future time, would be beneficial.

SUMMARY OF THE INVENTION

A system of the present invention receives information from a user, e.g., consumer, customer, patient, analyzes the information, and dispenses the following to a consumer based on inputs from the consumer, an insurance provider, a medical provider: a) healthcare products including, those that qualify for government reimbursement-eligible programs, such as health spending account (flexible spending account, health savings account, health reimbursement account) eligible products; b) medically pertinent patient, product, treatment, wellness and/or insurance (payment) related information; c) health-related diagnostic services; d) electronic payment (credit, debit or Flexible Spending Account (FSA) debit); e) health spending account balances and account management; f) electronic access to consumer purchase discounts, coupons and/or sweepstakes; product samples, and combinations of the above.

The system provides consumers with access to the features listed above in non-traditional venues (venues part of, adjacent to or apart from spaces that offer medical goods and/or services). The combination of all of these features is unique in a one-stop vending source. The consumer benefits from the convenience afforded by the invention since it provides a full range of services and easy access to product, diagnosis, medical information, payment, account management, discounts, samples and Consumer value opportunities.

DETAILED DESCRIPTION OF THE INVENTION

In particular, at a general level, the present invention is directed to a vending system or automated store and method of practice that has a means for inputting data, e.g., data input device, means for analyzing the data, e.g., microprocessor, and an output based on the analysis that includes information, product, or both.

Figure 1:
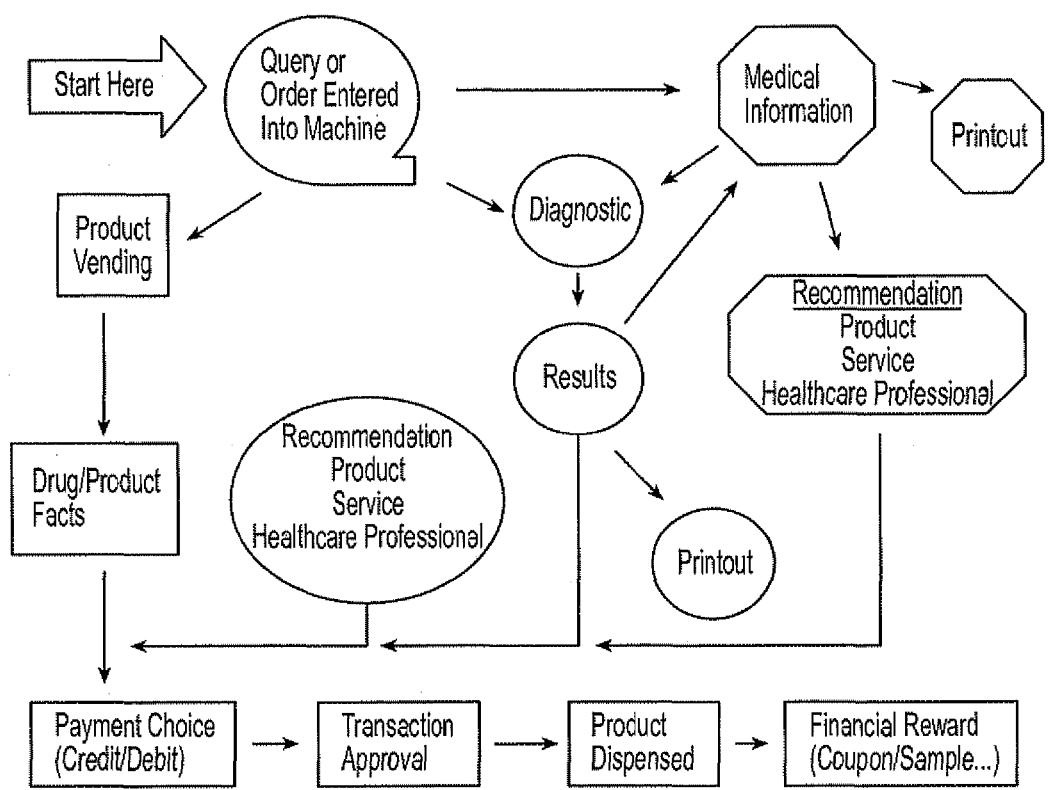
FIG. 1 is a schematic drawing of process steps for practicing one embodiment of the invention.

FIG. 1 is a process diagram illustrating the steps or activities performed in accordance with various embodiments of the present invention. In one embodiment, the vending system is capable of responding to a request for a specific product or to an inquiry from the consumer to identify an appropriate product or provide information on treatment options.

Figure 2:
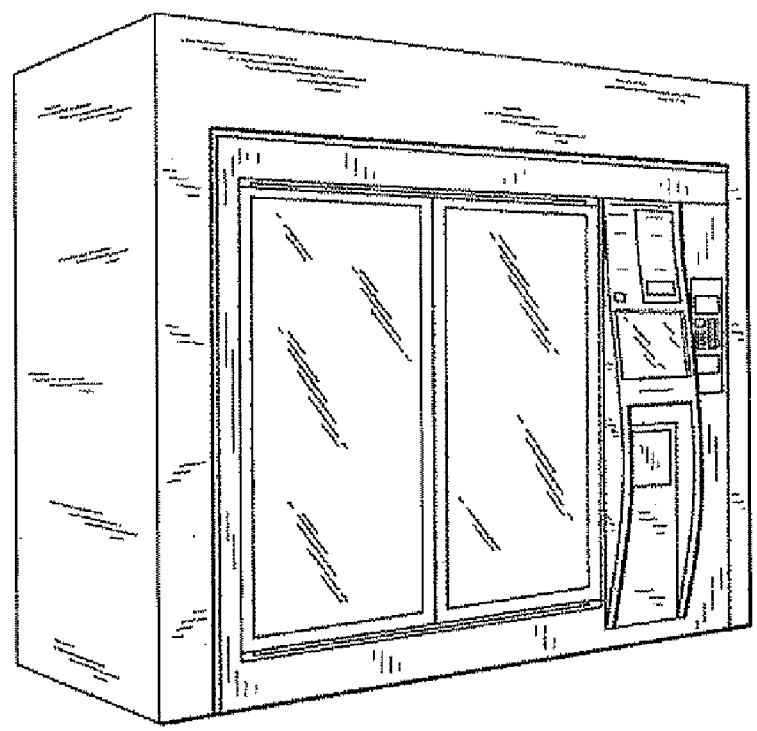
FIG. 2 is a perspective view of a preferred vending machine for practicing the present invention.

Vending machines designed to display and dispense products are known and commercially available. A particularly preferred vending machine for use as part of vending system or automated store is available from Zoom Systems under the trade name HealthZone24. An exemplary vending machine is illustrated in FIG. 2. Other configurations, set-ups and designs could be used for practicing the inventions described herein. The exemplary vending system consists of about 28 square feet of space available for inventory and display of product offerings. As described more fully below, consumers can interact with the vending system shown in FIG. 2 using a touch-screen and can make payments using a card swipe. Selected products are retrieved from inventory with a robotic arm that delivers the selected product to a dispensing door. The vending machine is centrally monitored, networked and controlled by a locally installed software system. Other vending machine designs could be utilized provided that appropriate means are available for communicating and networking with required processing systems described below.

The present invention is particularly suited for the delivery of personal or healthcare products. Examples of healthcare products, include but are not limited to: analgesics, anti-inflammatory agents, antiarthritics, anesthetics, antihistamines, antitussives, antibiotics, anti-infective agents, antivirals, anticoagulants, antidepressants, antidiabetic agents, antiemetics, antiflatulents, antifungals, antispasmodics, appetite suppressants, bronchodilators, cardiovascular agents, central nervous system agents, central nervous system stimulants, decongestants, oral contraceptives, diuretics, expectorants, gastrointestinal agents, migraine preparations, motion sickness products, mucolytics, muscle relaxants, osteoporosis preparations, polydimethylsiloxanes, respiratory agents, sleep-aids, urinary tract agents and mixtures thereof. Healthcare products contemplated for use in the present systems can also encompass self-diagnostic devices, such as pregnancy tests, cholesterol tests, viral and infection tests, and blood glucose monitors and test strips and related consumables for such diagnostic devices.

In the instance where the consumer wishes to purchase a specific product, the purchasing process begins when the consumer approaches the vending system and provides a means for identification, a means for payment or product selection. For purposes of identification, a consumer could provide personal, medical, insurance information or financial information, using an input device, e.g., touch screen, a card reader, keypad, biometric measurement device, or radio frequency tag. Upon selection of one or more specific products, the vending system can optionally provide the consumer with applicable product information in a view screen, text message, or in print form at the time the product is dispensed or prior thereto. A consumer may desire such product information prior to delivery of the product to ensure an appropriate selection has been made. The consumer can then either proceed to pay for the product in accordance with the previously entered payment means or select a means for payment at this time.

Payment options, include cash, credit cards, debit cards, radio frequency devices, coupons or similar means to electronically process payments. Systems for accepting and processing various forms of coin and paper currency are known in the art. Credit, debit or other electronic payment means generally require the vending system to connect or otherwise communicate with a central processing system for the applicable payment means to authorize such transactions in known fashion. Upon receipt of the transaction approval, the vending system dispenses the selected product to the consumer. The vending system can optionally also deliver a financial reward, such as a coupon, or other reward, such as product sample, for making a purchase. The reward can be provided at the time of purchase or subsequently in a separate communication. The reward can alternatively be provided to the consumer electronically, such as via an email letter, text message or maintained in the central database associated with the vending system for use with a subsequent purchase.

In an alternative embodiment, the payment means is associated with and executed through a savings account maintained for qualified purchases, such as over-the-counter or prescription healthcare products, deductibles, co-pays and health-care related services. Purchases from these accounts are typically undertaken to the extent these goods or services are not otherwise covered by an individual's health insurance plan. The vending system in such case would preferably connect or communicate with a processing center for such accounts. In similar fashion to a credit card authorization, the processing center would be responsible for authorizing the transaction and recording the transaction in the account records. One benefit of this process is that the consumer is not required to submit any paper work to secure reimbursement for the purchase. This advantage would be expected to improve reimbursement rates for the consumer and consequently increase the value of such accounts to consumers.

Examples of qualified savings accounts include, but are not limited to, health savings accounts, health reimbursement arrangement and health care flexible spending accounts. Each of these accounts are described below.

| | HSA—Health Savings Account | HRA—Health Reimbursement Arrangement | HCFSA—Health Care Flexible Spending Account |
|---|---|---|---|
| Legal Authority | Medicare Prescription Drug, Improvement, & Modernization Act of 2003 and supplemental guidance from the IRS | IRS Guidance 2002-45 | IRS code Section 125 |
| What expenses qualify for distribution? | Qualified medical expenses defined under §213(d) of the Internal Revenue Code (IRC), except for amounts distributed to pay health insurance premiums. HSAs can be used to pay premiums for (1) Temporary Continuation of Coverage (TCC), (2) Long Term Care Insurance (3) retiree health insurance premiums including Medicare after age 65 (4) health insurance premiums while receiving unemployment compensation and (5) over-the-counter medications. | Qualified medical expenses defined under §213(d) of the Internal Revenue Code (IRC) (including health care, over-the-counter medications, Medicare insurance premiums and qualified Long Term Care Insurance premiums) except for medical expenses explicitly prohibited from reimbursement by FEHB law. | Qualified medical expenses defined under §213(d) of the Internal Revenue Code (IRC), except for amounts paid for health insurance premiums and Long-Term Care Insurance premiums, but including most over-the-counter medicines and products. |

In a further alternative embodiment, rather than requesting a specific product or products from the vending system, a consumer provides information or queries the vending system to identify an appropriate product or treatment. For example, the consumer can provide the vending system with a description of symptoms for which treatment is sought. The consumer can select from a list of symptoms generated by the vending system. Alternatively, the consumer can enter a general description of symptoms using a keyboard or other means for communication from which the vending system use appropriate search algorithms or similar means to identify one or more appropriate products from a database.

The vending machine would then send the information either to another machine or processing center for analysis or analyze the inputted information using an onboard computer and software. The database can be installed remotely in the memory at each vending machine and updated centrally or updated manually in the same fashion that the inventories of products are replenished. Alternatively, the database can be centrally located and maintained provided that a means for connecting with and communicating with the central location database is available. The vending machine can communicate and connect with such a database or central monitoring system via a hard-wire connection, satellite transmission, local radio transmission, utilizing so-called Wi-Fi network connections or combinations thereof.

After analysis of the information, the vending system provides an output that in the form of a recommendation or suggestion for an appropriate product or products to treat the condition/symptom(s). The vending system can also recommend alternative treatments option in the event that one or more products are not available at that particular vending machine. The vending system can also recommend an appropriate means of payment for the product(s) based on available insurance and account information (including those savings accounts mentioned above), inform the consumer of any eligible discounts or coupons for the chosen product or related products. The vending system can also display drug product facts electronically or in printed paper form. Drug product facts may include but are not limited to dosing information, dosing directions, warnings, potential side effects, counter indication information, active and inactive ingredients, amount(s) of active ingredient(s), manufacturer identification information, patent identification, information on when to ask or contact a doctor, storage information, and product expiry information.

Optional features include symptom matching with products that treat specific symptoms. Additional optional features include the ability to make changes to a Flexible Spending Account or Health Savings Account just prior to purchase. For example, cough, fever, headache, toothache inputs would be matched to a cough, fever, headache or analgesic product. The consumer would pay for the product and the machine would automatically reimburse the consumer for the purchase. The system also allows for the consumer to access information about specific health accounts, and the ability to ask questions and receive answers from the system regarding how those accounts work.

Any actual medical condition diagnosis must be performed by a health professional, who could be connected real-time to an array of machines and have online discussions with patients in an effort to provide as accurate diagnosis as possible.

In another embodiment the vending system has optional displays, which can retrieve data from a database, or card that shows a history of health conditions or health file information associated with a particular individual. These selections would narrow the range of conditions based on past history. The patient would have the option of pointing to or selecting their particular condition (i.e. 1. allergy, 2. headache, 3. back pain, 4. other) on a touch screen or other input device and have the appropriate treatment recommended. The individual could then select the desired treatment, or product options and the appropriate product could be delivered through the vending machine.

In a still further embodiment, the vending system can include features for measuring or monitoring symptoms. Examples of the types of symptoms that can be monitored by such a vending system include, for example, body temperature, blood pressure, blood glucose levels and cholesterol levels. Machine and systems are commercially available for measuring blood pressure of consumers in retail spaces or at home. Similarly, devices are commercially available to measure body temperature, such as infrared monitors. Glucose monitors are commercially available, such as the One Touch meters from LifeScan. Individual test kits are also known and available to test total cholesterol. The results of these tests can be directly measured by the vending system or entered by the consumer using the devices described above.

In an alternate embodiment the vending system is connected to a system that can mechanically dispense prescription pharmaceutical products from a bulk container into appropriate packaging from a bulk container.

The invention is unique from prior art since it provides a full array of goods and services. This vending source will communicate information electronically from externally databases.

I claim:

1. A vending system comprising at least one vending machine, each vending machine having:
   a. data input means for receiving information from an individual;
   b. an inventory of one or more products available for purchase;
   c. a dispensing means for retrieving one or more products from the inventory and delivering such product(s) to a retrieval point; and
   d. a payment means for selecting and providing payment for one or more selected products; and
   e. communication means for accessing a database containing information relating to the products in inventory,
   wherein the vending system has a database suitable for recommending one or more products appropriate for treating symptoms entered by the individual and is capable of delivering product information relating to the use of products selected by the individual prior to or simultaneously with the delivery of the product(s).

2. A vending system according to claim 1 wherein the information is selected from the group consisting of identification, payment method, insurance carriers, healthcare provider, symptoms, one or more desired products and combinations thereof.

3. A vending system according to claim 1 wherein the products are personal care or healthcare products.

4. A vending system according to claim 3 wherein at least some of the personal care or healthcare products are packaged in containers holding other than individual dose quantities.

5. A vending system comprising at least one vending machine, each vending machine having:
   a. data input means for receiving information from an individual;
   b. an inventory of one or more healthcare products that are packaged in containers holding other than individual dose quantities available for purchase;
   c. a dispensing means for retrieving one or more products from the inventory and delivering such product(s) to a retrieval point; and
   d. a payment means for selecting and providing payment for one or more selected products;
   wherein the vending system has a database suitable for recommending one or more products appropriate for treating symptoms entered by the individual and is in communication with a central system that authorizes transactions or processes payments for a selected purchase by the individual.

6. A vending system according to claim 5 wherein the information is selected from the group consisting of identification, payment method, insurance carriers, healthcare provider, symptoms, one or more desired products and combinations thereof.

7. A vending system according to claim 5 wherein the vending machine delivers a reward for making a purchase.

8. A vending system according to 7 wherein the vending system delivers the reward electronically to the individual.

9. A vending system according to claim 5 wherein the central system authorizes payments for purchases from a qualified savings account associated with the individual.

10. A vending system according to claim 9 wherein the qualified savings account is only authorized for purchasing health-care related goods or services not otherwise covered by health insurance.

11. A vending system comprising at least one vending machine, each vending machine having:
- a. a data input means for receiving information from an individual;
- b. an inventory of one or more products available for purchase;
- c. a dispensing means for retrieving one or more products from the inventory and delivering such product(s) to a retrieval point;
- d. a payment means for selecting and providing payment for one or more selected products; and
- e. a communication means for accessing a database containing information relating to the products in its inventory,
- wherein the consumer provides the vending system with a description of symptoms for which treatment is sought and the vending system provides a recommendation of one or more products appropriate for treating such symptoms.

12. A vending system according to claim 11 wherein the information is selected from the group consisting of identification, payment method, insurance carriers, healthcare provider, symptoms, one or more desired products and combinations thereof.

13. A vending system according to claim 11 wherein the vending system analyzes products available in its inventory and provides a recommendation of one or more products that are currently in its inventory for treating the identified symptoms.

14. A vending system according to claim 11 wherein the vending system using the database relating to the use of products to produce a recommended product or products.

15. A vending system according to claim 14 wherein the database is stored remotely at a central location that is in communication with the vending machine.

16. A vending system comprising at least one vending machine, each vending machine having:
- a. a data input means for receiving information from an individual;
- b. an inventory of one or more products available for purchase;
- c. a dispensing means for retrieving one or more products from the inventory and delivering such product(s) to a retrieval point; and
- d. a payment means for selecting and providing payment for one or more selected products;
- e. communication means for accessing a database containing information relating to the products in inventory, and
- f. one or more diagnostic devices for humans;
- wherein the one or more diagnostic devices deliver output information and the vending system provides a recommendation of one or more products appropriate for treating such symptoms.

17. A vending system according to claim 16 wherein the information provided by the consumer is based at least in part on the output information from the diagnostic devices.

18. A vending system according to claim 16 wherein the output information from one or more diagnostic devices is delivered directly to the vending system.

19. A vending system according to claim 16 wherein the information from the individual includes additional further physical condition information.

20. A vending system according to claim 16 wherein at least some of the information or the output information relates to physical conditions of the individual selected from the group consisting of body temperature, cholesterol levels, blood glucose levels, blood pressure and combinations thereof.

* * * * *